United States Patent
Colic

(10) Patent No.: US 6,544,401 B1
(45) Date of Patent: Apr. 8, 2003

(54) BIOMIMETIC WATER SOLUTIONS AND COMPOSITIONS, THEIR USE AS AND IN HEALTH AND BEAUTY CARE PRODUCTS AND THE METHODS TO PREPARE THEM

(75) Inventor: Miroslav Colic, Goleta, CA (US)

(73) Assignee: Henceforth Hibernia, Inc., New York, NY (US)

( * ) Notice: Subject to any disclaimer, the term of this patent is extended or adjusted under 35 U.S.C. 154(b) by 0 days.

(21) Appl. No.: 09/560,517

(22) Filed: Apr. 28, 2000

Related U.S. Application Data

(60) Provisional application No. 60/131,557, filed on Apr. 29, 1999.

(51) Int. Cl.[7] .............................................. A61K 7/075
(52) U.S. Cl. ........................ 205/400; 205/556; 205/618; 424/401; 424/450
(58) Field of Search .................................. 205/400, 556, 205/618; 424/401, 450

(56) References Cited

U.S. PATENT DOCUMENTS 6,120,758 A * 9/2000 Siddiqui et al. ......... 424/78.02
6,221,389 B1 * 4/2001 Cannell et al. ............... 424/45

* cited by examiner

Primary Examiner—Arun S. Phasge
(74) Attorney, Agent, or Firm—Cohen, Pontani, Lieberman & Pavane

(57) ABSTRACT

The invention is directed to compositions of health and beauty care products which are produced by mimicking the human body's own defense mechanisms and the methods to produce and use such compositions. The products are water based, oil and surfactant free and can be antimicrobicidal, without causing drying or itching of the skin. Moreover, such products enhance hydration and moisturizing of the skin and prevent itching. The products are based on water solutions of mixed oxidants, mimicking those produced by the human immune system cells. The invention also describes the processes for producing such products. Such products can be used independently, or to prepare creams, gels, lotions, tooth and other pastes, powders, suppositories, body and hair shampoos and rinses, oral and body hygiene rinses, creams and other products which would be obvious to those skilled in the art.

10 Claims, No Drawings

BIOMIMETIC WATER SOLUTIONS AND COMPOSITIONS, THEIR USE AS AND IN HEALTH AND BEAUTY CARE PRODUCTS AND THE METHODS TO PREPARE THEM

RELATED APPLICATIONS

This application claims priority from U.S. Provisional Patent Application Ser. No. 60/131,557 which was filed on Apr. 29, 1999. The provisional application No. 60/131,557 is hereby incorporated by reference in its entirety.

BACKGROUND OF THE INVENTION

1. Field of the Invention

The invention describes novel aqueous compositions for microbicidal health and beauty care products and the methods for their preparation and use.

2. Description of the Related Art

Health and beauty care products have been an important part of the human civilization from its beginnings. The health and beauty care products include skin, hair, scalp, tooth, mouth, feminine hygiene and other relevant cosmetics as well as "over the counter" health care products. One of the imperatives of modern health and beauty care products is to provide antimicrobicidal ingredients along with the other wanted actions, such as improved hydration, moisturizing, antioxidant and anti-itching activities. This is actually very difficult to achieve.

Among the common ingredients of health and beauty care products, alcohols, are the ones most frequently used. Alcohols provide microbicidal action and are a good solvent for most other ingredients. On the other hand, alcohols cause drying and itching of the skin and mucosa. Other commonly used agents result in even stronger, unpleasant side effects. Benzoyl peroxide is, for instance, a common ingredient of acne fighting products. It has an unpleasant smell and taste and also irritates the skin. Moreover, it leaves bleached spots on clothes. Retin A, a recent development in acne and wrinkle fighting, also irritates and overdries the skin. Beta-hydroxy acids have similar side effects.

Inorganic microbicidal agents have also been described and used in beauty care products. Hydrogen peroxide has been the most popular one. Other agents which slowly release nascent oxygen have also been described. (See, for instance, U.S. Pat. Nos. 5,736,582; 5,653,994 or the book "Oxygen Therapies," by Ed McCabe; Energy Publications, Morrisville, N.J., (1988).) Yet all such reagents cause skin and mucosa irritation. In most uses, hydrogen peroxide was used with surfactants, oils and other ingredients. This was needed to wet the skin or mucose to a determined level (agents like surfactants are needed to lower the surface tension). (See, for instance, U.S. Pat. Nos. 4,900,721; 3,954,974; 5,773,402). The aforementioned patents and publication are hereby incorporated by reference in their entireties.

Chlorine based oxidants have also been proposed for microbicidal beauty care products. The evident problems of such products are unpleasant smells, bleaching of clothes and, in many cases, the low chemical stability of the products. Such products also dry and irritate the skin.

Chlorine dioxide solutions have been the most popular ones. See, for instance, U.S. Pat. Nos. 4,737,307; 5,738,840; 4,317,814. The contents of which are hereby incorporated by reference in their entireties.

Mixtures of chlorine based oxidants and oxygen based oxidants were also described. Yet, like other previously mentioned products, such mixtures also dry the skin, have unpleasant odor and bleach clothes. None of the above mentioned products ever achieved a wide popularity among consumers. See, for instance, U.S. Pat. Nos. 4,574,084; or 4,552,679, the contents of which are hereby incorporated by references in their entireties.

Remarkably, our own bodies also use mixed chlorine based-oxygen based systems to kill microbes and save the skin and the rest of the body from microbial infestation. Yet, healthy human individuals do not show permanent symptoms of skin drying or irritation. The chemical compositions used by our body to protect itself do not show such side effects. The enzyme myeloperoxidase produces the mixture of hydrogen peroxide and hypochlorous acid at a pH close to that of the skin (around pH 5). Such mixtures are extremely efficient in killing various microbes. The detailed mechanisms and efficiency of microbicidal action of these mixtures were recently reviewed (J. K. Hurst, "The Role of Inorganic Chemistry in Cellular Mechanisms of Host Resistance to Disease," in Electron Transfer Reactions, American Chemical Society, Washington, D.C., (1997).) The above mentioned publication is hereby incorporated by reference in its entireties.

SUMMARY OF THE INVENTION

The object of the present invention is to provide improved health and beauty care products based on imitating or mimicking—hence the term "biomimetic"—nature's own ways of yielding microbicidal protection without any significant adverse side effects. Moreover, the object of this invention is to provide improved products which will actually promote hydration of the skin and prevent itching and irritation while giving maximum microbicidal protection. A further object of this invention is to provide water based health and beauty care products with minimum amounts of oils or surfactants, or in the preferred embodiment, without any oil, surfactant or alcohol.

In accomplishing these and other objects of this invention, there are provided methods for producing such water based health and beauty care products. There are also disclosed methods of using the products described in this invention as a mixture with other health and beauty care products such as creams, gels, lotions, powders, tooth and other pastes, suppositories, body and hair shampoos and rinses, oral hygiene rinses and other products which will become apparent to those skilled in the art.

In the first method of producing biomimetic hair, body and skin care products, electrochemistry (especially membrane based electrolysis systems) is used to produce activated water with numerous different chlorine based oxidants at the desired pH. Hydrogen peroxide is then added to that solution and the pH is adjusted to the desired value. Catalytic chlorine filters or air sparging devices can be used to remove excess free chlorine. This removes unpleasant smells and unwanted free chlorine reactions with the skin. The solutions can be sparged with oxygen to yield needed oxygen to the skin.

In the second method of producing the biomimetic hair, body and skin care products, the desired amount of hypochlorous acid/hypochlorite is added to the solution and the pH is adjusted. Ozone can then be introduced to that solution. After the equilibration, hydrogen peroxide can be added, and the pH adjusted to the desired value. Once again, the excess free chlorine can be removed with catalytic chlorine filters and/or air sparging devices.

In yet another aspect of the invention, methods are described to prepare lotions for hair, body and skin care products or hair care products or other beauty and health care products. Such lotions have biomimetically prepared water as the main ingredient.

In yet another aspect of the invention, methods are described to prepare gels for hair, body and skin care products or other beauty and health care products with the minimal or no use of any oil, surfactant and fat.

In yet another aspect of the invention, methods are described to prepare suppositories for the feminine hygiene and yeast infection treatment.

In further aspect of the invention, methods are described to prepare oil and surfactant containing beauty and health care products, such as shampoos, creams or suntanning products, by using biomimetically produced water solutions.

In another aspect of the invention, methods are described to prepare tooth paste or oral rinse hygiene products which are based on biomimetically produced water.

Other objects and features of the present invention will become apparent from the following detailed description considered. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

An object of this invention is to avoid the above mentioned shortcomings of the current hair, body and skin care products. An oil free, water based hair, body and skin care product line with stable, reliable and skin friendly compositions and the methods to prepare them are described. According to the invention, water based mixtures of oxidants with compositions are prepared mimicking those inside the immune system cells of human body. Such compositions are then used to prepare gels, shampoos, creams, rinses, lotions, ointments, pastes, powders or other over the counter beauty and health care products.

The mechanism of action of phagocytic white cells upon encountering bacterium or other pathogens involves a series of biochemical transformations that lead to the isolation and killing of the pathogen. Among those changes, the activation of a respiratory chain, which produces a series of oxygen carrying oxidants such as superoxide ions, hydrogen peroxide, hydroxyl radicals, singlet oxygen and chlorine oxygen compounds such as hypochlorite, plays a major role. (J. K. Hurst, "The Role of Inorganic Chemistry in Cellular Mechanisms of Host Resistance to Disease," in Electron Transfer Reactions, American Chemical Society, Washington, D.C., (1997)). The above mentioned publication is hereby incorporated by reference in its entirety. It was subsequently found that reactive nitrogen compounds such as nitric oxide and peroxynitrite also play a role in the host defense mechanism. The main component of this defense mechanism is hypochlorite ion $ClO^-$. Other oxidant such as peroxide, stabilize and enhance the reactivity of hypochlorite. The reactions between hypochlorite ions and hydrogen peroxide also produce high energy hydroxyl radicals and singlet oxygen. (L. P. Candeias et al., FEBS Letters, Vol. 333, pp. 151–153 (1993); A. U. Khan and M. Kasha, Proc. Natl. Acd. Sci. USA, Vol. 91, pp. 12362–12364 (1994).) The contents of these publications are hereby incorporated by reference in their entireties. Such phagocytic cells defend human skin from the ever-present pathogens. Yet healthy human individuals do not feel discomfort, skin dryness or itching. Through the years of evolution, an microbicidal system which is not irritating to the host developed. Such mixtures are also a very efficient microbicidal agent, which surpasses pure hypochlorite by almost a factor of one hundred. (Wilk, L. J. et al., The Science of the Total Environment, Vol. 63, pp. 191–197 (1987).) This publication is hereby incorporated by reference in its entirety.

Methods of Preparation of Biomimetic Water Solutions

The term "biomimetic water solution" means the product naturally produced by human body or by either of the processes described as following.

The human bodies use electrochemistry and catalytic processes to produce such compositions. Similar approaches are used in this invention.

In the first method of producing biomimetic beauty and health care products, electrochemistry (especially membrane based electrolysis systems) is used to produce activated water with numerous different chlorine based oxidants at the desired pH. Hydrogen peroxide is then added to that solution and the pH is adjusted to the desired value. Catalytic chlorine filters or air sparging devices can be used to remove excess free chlorine. This removes unpleasant smells and unwanted free chlorine reactions with the skin. The solutions can be sparged with oxygen to yield needed oxygen to the skin.

Electrochemical devices needed to produce activated water with a mixture of chlorine based oxidants are, for instance, described in U.S. Pat. Nos. 5,833,831; 5,674,537; 5,788,820, or in Y. Shiramizu et al., J. Electrochem. Soc., Vol. 143, pp. 1632–1635 (1996); which are hereby incorporated by reference in their entireties. Such devices can operate batch or continuous. Water to be electrolyzed should be purified, as by deionization, reverse osmosis or distillation, as any ions which are free radical scavengers such as carbonates can interfere with the electrolysis process. To increase the conductivity of purified water, sodium chloride or potassium chloride may be added. The concentrations of added chlorides can vary between 10 mg/l and 10 g/l. In batch devices, the cathode and anode areas are then filled with the same amount of chloride solution and the equipment is closed. The electrolysis is then started and can last for between 10 seconds and 30 minutes. The water from the anode compartment of such devices is then collected and used for further treatment. The pH of such water can vary between 0.8 and 6. The redox potential of such water can vary between 1300 mV and 650 mV. If long term stability is needed, the best results are achieved with the water with pH around 5.5 and redox potential around 750 mV. Such water is stable for more than one year. Alternatively, sodium or potassium chloride solutions can be connected to the flow-through device. Such devices perform the electrolysis instantaneously. Once again, water from the anode compartment is collected. Such water also shows the best results when used around pH 5.5 and redox potential of 750 mV. For the best results, the equipment manufacturer's instructions should be followed.

Various amounts of hydrogen peroxide is then added to such activated or electrolyzed water collected from the anode compartment. A concentration between 10 mg/l and 100 mg/l can be used without interfering with the stability of the solution. Upon the addition of hydrogen peroxide, the pH should be adjusted to about 5.5. The activity of such water towards various microorganisms with standard techniques known to those skilled in the art should be tested as a major quality control procedure.

The next step in the production of biomimetic water is removal of excess free chlorine from the water. This can be achieved by air sparging with any of the available commercial devices which are well known to those skilled in the art and are, by way of examples, described in "Water Quality and Treatment; A Handbook of Community Water Supplies", (F. W. Pontius editor; McGrawHill, New York, N.Y. (1990).) This book is hereby incorporated by reference in its entirety. The residual free chlorine can then be removed with catalytic chlorine filters as is well known. The details of such filtration are also described in the above mentioned Pontius book. The water is then ready for the preparation of skin, beauty and health care products. Numerous variations of this process such as, for example, different pH values of the final water solutions, different peroxo agents or other methods of free chlorine removal would be obvious to the skilled in the art and are, therefore, encompassed by this patent.

In the second method of producing the biomimetic hair, body and skin, beauty and health care products, the desired amount of hypochlorous acid/hypochlorite is added to the solution and the pH is adjusted in any well known manner. Ozone can then be introduced to that solution. After equilibration, hydrogen peroxide can be added, and the pH adjusted to a desired value. Once again, the excess free chlorine can be removed with the catalytic chlorine filters and/or air sparging devices. Reaction of ozone and hypochlorite will yield similar products as the electrolysis of sodium chloride.

The advantage of the second method of preparation of biomimetic water solutions is that all water can be used, unlike the electrolysis based process which is bound to lose the half of the water electrolyzed in the cathode area. In the second method, one also needs purified water (e.g. water that is deionized, reverse osmosis purified or distilled). Sodium hypochlorite is then added at concentrations between 1 mg/l and 1000 mg/l to the purified water. The water pH is then adjusted with HCl to around 5. After 15 minutes of stirring and equilibration, ozone is then introduced to such solution with vigorous stirring. Ozone can be produced by any of the commercial devices such as, for example, is described in the aforementioned book, the contents of which have already been incorporated by reference in their entirety. The concentrations of ozone used are to be between 0.1 mg/l and 3 mg/l. Higher amounts of ozone will produce unstable solutions. After 30 minutes of stirring, the pH is then adjusted to about 5.5 with the addition of such pH adjusters as HCl or NaOH and the solution is ready for further processing, which is identical to that of the first method. The addition of hydrogen peroxide to final concentrations between 1 and 100 mg/l is followed by air sparging to remove free chlorine and filtration with the catalytic chlorine filters. Such water solution is then ready for the preparation of the beauty and health care products. Water prepared with either method 1 or 2 will be termed "biomimetic water solutions" in the remaining part of the text of this patent. Numerous modifications of this process (other values of pH, ionic strength, type of peroxo agent used etc.) are obvious to the person skilled in the art.

EXAMPLES

Example I

Lotions

The above described biomimetic water solutions with pH around 5.5 and redox potential of around 750 mV is used as a main ingredient of a cleansing lotion. The lotion can be used for morning and evening skin cleansing, or at any other time such as, before the use of other skin care components. It can also be used as an antimicrobial skin care lotion. The lotion also enhances hydration and moisturizing of the skin and is useful as a moisturizing lotion used when there is exposure to the sun or wind. The lotion also provides a soothing effect after insect bites, shaving, or other skin abrasion or irritant or mild allergies. Aloe vera and other herbal products can be added to the lotion at various concentrations. Other additives such as fragrances, surfactants, antibiotics, humectants, antimicrobial agents, pain relief agents, anti-inflammatory agents etc. can be added to the lotion for a particular use. Such modification will be obvious to those skilled in the art. The use of oil and emollients with such lotions is not recommended.

Example II

Gels

The main component of the gels will once again be biomimetic water solutions with pH around 5.5 and redox potential around 750 mV. Such water solutions will be used at concentrations between 40% and 99%. Additional gel ingredients such as for example, thickening agents, humectants, emollients, pharmaceutically active agents, vitamins, antioxidants, herbal extracts and other possible active or inactive supporting ingredients which would be obvious to those skilled in the art may be included.

Various thickening agents may be used to adjust the viscosity of gels. Hydrophilic, oil free gelling agents which are stable at low pH are the preferred ingredients of such gels. The gelling agents preferably will have a viscosity of between 1000 cps and 50000 cps (1% aqueous solution at 20 degrees Celcius, as measured with standard Brookfield RVT viscosimeter). The gelling agent will be used at concentrations between 0.01% and 5 wt %. The most suitable hydrophilic gelling agents which are stable at low pH are cellulose ethers (e.g. hydroxyethylcellulose, hydroxypropylcellulose, carboxymethylcellulose), guar gums, xantan gum and other polysacharides. The preferred gelling agents used in this invention is hydroxyethylcellulose. Other gelling agents such as polyacrylic based and polyacrylamide based gelling agents can also be used but this requires the addition of oils, alcohols and other organic ingredients. Other hydrophilic gelling agents including clays such as bentonite or hectorite may also be included.

The compositions also can contain one or more humectants, which will further enhance the moisturizing ability of the gel. Humectants will typically be present at concentrations between 0.1% and 30%. The most preferred humectants to be used in the gels are polyhydroxyalcohols, such as propylene glycol, glycerin, sorbitol, hexanetriol, hexylene glycol, sugar, and starch derivatives, hyaloronic acid, lactamide, ethanolamines, etc. Natural humectants such as aloe vera can also be used. The preferred humectants used are polypropylene glycol at 1–4% and glycerin at 1–3%. All percentages are expressed as percentage of the weight of the composition (1%=1 g of humectants in 100 grams of product).

Other active ingredients such as fragrances, stabilizers, emulsifiers, metal chelating agents, or additional solvents can be added. Pharmaceutically active ingredients include, but are not limited to, any chemical or herbal material or compound which is suitable for topical administration and delivers any desired effect. Such agents are present at concentrations between 0.1 and 30 wt %. Such agents include sunscreen agents, antimicrobial agents, anti-acne agents, anti-inflammatory agents, skin bleaching agents, wound dressing and healing agents, antiitching agents, anti-cancer agents and many other agents which will be obvious to those skilled in the art.

Antioxidants and vitamins, either antioxidants or non-antioxidants which would enhance nourishing of the skin and prevent photoaging and oxidative damage to the skin can also be added. Thiol antioxidants such as N-acetylcysteine, pyrrolidine dithiocarbamates, lipoic acids, or their salts, acid or bases, can be used. Other antioxidants such as vitamin C, E or A can be used. Natural antioxidants such as green tea, Gingko Billoba or grape seed extracts can also be used. Synthetic antioxidants such as SOD mimetics or catalase mimetics can also be used. Any other compound or material with antioxidants properties can be used. Other vitamins such as B12, B6, D, or folic acid can also be added to the gel. Those skilled in the art will find that many other vitamins and antioxidants not mentioned here can be used.

Anti-acne drugs and herbal extracts can be added to enhance the antimicrobial effects of the gels. Salicilic acid, glycolic acid, resorcinol, N-acetylcysteine, retinoic acid and derivatives, antibiotics and hydroxy acids (alpha or beta) can also be added. Numerous other anti-acne agents, well known to those skilled in the art can be added. Emollients can be added but the use of oils is not preferred. However, emollients such as volatile silicone oils, non-volatile silicone oils or other known compounds can be added to the gels.

The compositions of some characteristic gels are specified below. It should be apparent to those skilled in the art that they are only examples of numerous other active compositions to prepare the gels.

| Moisturizing/after Sun/after shower/after shave gel | |
|---|---|
| Biomimetic water solution | 94% |
| Hydroxyethylcellulose | 1% |
| Propylene glycol | 3% |
| Glycerin | 1% |
| Aloe vera | 0.5% |
| EDTA | 0.01% |
| lidocaine hydrochloride | 0.5% |
| fragrances (optional) | 0.1% |

Mild heating (around 60 degrees Celsius and stirring with multiple blade mechanical stirrer (400 rpm) was used to dissolve hydroxyethylcellulose and form a gel. The gelling agent powder should be added slowly into the vortex to avoid clumping. Hydroxyethylcellulose was dissolved into biomimetic water solution at 1 wt %. Propylene glycol (3%), glycerin (1%), aloe vera (0.5%), EDTA (0.01%), and lidocaine (0.5%) were then added while mixing with the mechanical stirrer. The formed gel was allowed to cool down to room temperature before packaging. Alcoholic solutions of desired fragrance were added, as an option.

In tests with 20 informed volunteers, 16 preferred such products to other after sun or moisturizing gels. Such gels did not leave a residue on the skin and it was easy to remove every drop of the gel from the bottle, unlike other products currently available. The gel was also efficient in reducing itching from dry skin, insect bites or acne prone skin.

Such a gel with the addition of N-acetylcysteine (2%), echinacea extract (0.1%) and salicilic acid (1%) was used as an anti-acne gel. Beta hydroxy acids (2%) can be added to enhance keratolytic gel properties. In tests with 15 informed volunteers, a significant reduction in the number of comedones and their surrounding inflammed area was achieved after ten days of using the gel. No itching, discomfort or overdrying of skin was observed.

OTHER EXAMPLES

Biomimetic water solution can also be used to prepare shampoos, whole body washes, creams and tooth and other pastes and powders. It enhances the antimicrobial properties of such products and also enhances a soothing feeling to the skin after the use of such products. Biomimetic water solutions thickened into a gel with the desired amount of hydroxyethylcellulose can also be used to fill suppositories for yeast infection/feminine hygiene products. For such applications, purified water currently used to manufacture those products is replaced with the biomimetic water solution. Actual methods for preparing the above mentioned health and beauty care products (shampoos, oral rinse solutions, creams, tooth paste etc.) are described in more details in, for example, Remington's Pharmaceutical Science, 15th Ed., Mack Publishing Company, Easton, Pa. (1980). Such methods are well known to those skilled in the art. Another well known source of information on preparation of health and beauty care formulations is, for example, Sagarin, Cosmetics Science and Technology, 2nd Edition, Volume 1; Wiley Interscience (1972). The above mentioned publications are hereby incorporated by references in their entireties.

More efficient delivery of the biomimetic water solution deeper into the skin or mucosa can be achieved in many ways. Small lipid vesicles known as liposomes can be used as carriers, as described in G. Gregoiraidis, Trends Biotechnol., Vol. 13, pp. 527–537 (1995). This publication is hereby incorporated by reference in its entirety. Water is then encapsulated within the liposome vesicles along with the other active ingredients. Such liposomes can, for instance, be used as a spray for the treatment of upper airways infections. Longer lived liposomes can be produced by attaching the polyethyleneglycol chain as described in Gregoiraidis, cited above. The particle size of the liposome will generally be in the range between 1 and 500 microns. Liposomes can also be used for the transdermal or oral biomimetic water solutions delivery.

Numerous stimuli can be used to enhance the transdermal transport of biomimetic water solutions, such as ultrasound, electromagnetic, electric or plasma pulses. (R. Langer, Nature, Vol. 392, suppl., pp. 5–10 (1998). The contents of this publication is hereby incorporated by reference in its entirety. Such stimuli can for instance be applied directly at the spot where acne are present in order to enhance the delivery of biomimetic water solutions with other medications.

Thus, while there has been shown and described and pointed out fundamental novel features of the invention as applied to a preferred embodiment thereof, it will be understood that various omissions and substitutions and changes in the form and details of the described compositions, and their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A health and beauty care product, comprising a biomimetic water solution, wherein said biomemetic water solution is produced by a process comprising the steps of:
   a) introducing sodium hypochlorite into purified water;
   b) adjusting the pH of said sodium hypochlorite solution to about 5.0;
   c) mixing ozone with said sodium hypochlorite solution resulting from step b to produce free chlorine and hypochlorite ions;
   d) introducing hydrogen peroxide into the solution resulting from step c; and
   e) removing said free chlorine from the solution resulting from step d to produce said biomimetic water solution;
   or by a process comprising the steps of:
   a) electrochemically activating a solution containing purified water and sodium or potassium chloride to produce free chlorine and hypochlorite ions by electrolyzing said solution in a device having a cathode compartment and an anode compartment;
   b) collecting the activated solution from said anode compartment;
   c) introducing hydrogen peroxide into said collected solution;
   d) adjusting the pH of the solution resulting from step c to about 5.5; and
   e) removing said free chlorine from the solution resulting from step d to produce said biomimetic water solution.

2. The health and beauty care product of claim 1, further comprising a pharmaceutically active ingredient selected from the group consisting of anti-acne, anti-inflammatory, pain relieving, antimicrobial, anti-itch, wound healing, antioxidant, scar remediating, and anticancer pharmaceutical components.

3. The health and beauty care product of claim 1, wherein said product is made in the form of a gel.

4. The health and beauty care product of claim 3, wherein said gel comprises 40–99% of said biomimetic water solution.

5. The health and beauty product of claim 4, wherein said gel comprises 94% of said biomemetic water solution.

6. The health and beauty care product of claim 1, wherein said product is made in the form of a lotion.

7. The health and beauty care product of claim 1, wherein said product is made in the form of a cream.

8. The health and beauty care product of claim 1, wherein said product is made in the form of an ointment.

9. The health and beauty care product of claim 1, wherein said product is made in the form of a shampoo.

10. The health and beauty care product of claim 1, further comprising liposomes.

\* \* \* \* \*